United States Patent [19]

Firth

[11] 4,305,275
[45] Dec. 15, 1981

[54] CHROMATOGRAPHIC APPARATUS AND METHOD OF OPERATION

[75] Inventor: Francis G. Firth, Los Angeles, Calif.

[73] Assignee: Applied Plastics Co., Inc., El Segundo, Calif.

[21] Appl. No.: 153,713

[22] Filed: May 27, 1980

[51] Int. Cl.³ .................................. G01N 31/08
[52] U.S. Cl. ......................................... 73/23.1
[58] Field of Search ............. 73/23.1, 61.1 C; 55/67, 55/197

[56] References Cited

U.S. PATENT DOCUMENTS

| | | | |
|---|---|---|---|
| 3,369,874 | 2/1968 | Wilhelm | 55/197 X |
| 3,677,066 | 7/1972 | King, Jr. et al. | 73/23.1 X |
| 3,949,806 | 4/1976 | Dunges | 55/67 X |

Primary Examiner—Jerry W. Myracle
Attorney, Agent, or Firm—William W. Haefliger

[57] ABSTRACT

Improvements in chromatographic column construction, resulting in facilitating packing techniques, and preparation. Use of improved column in analytical and preparative chromatographic applications produces higher efficiencies, lower solvent pressures, faster throughput, and improved resolution of components.

Column construction is such, that mechanical energy can be applied longitudinally to the column outer surface, to produce standing waves or controlled vibrations in the packing. The applied energy is in the preferred form of sonic or ultrasonic vibrations.

28 Claims, 10 Drawing Figures

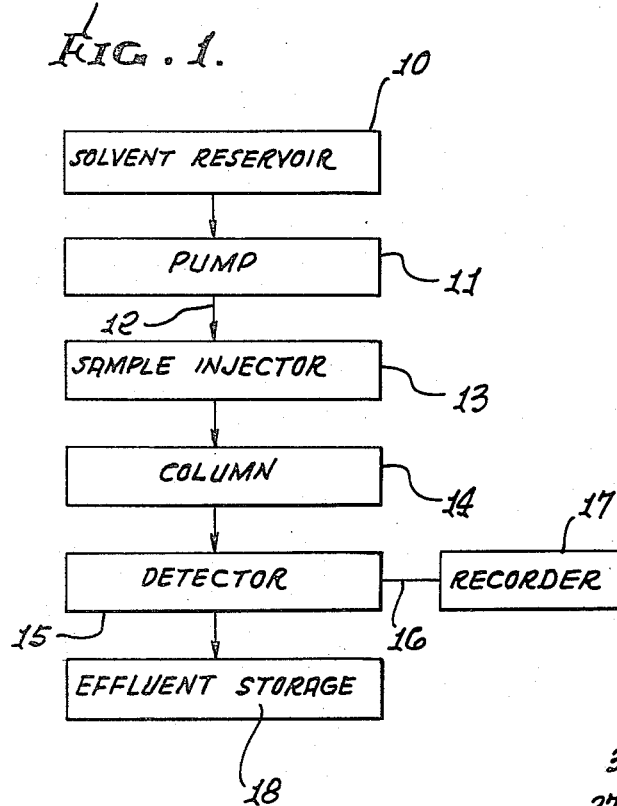
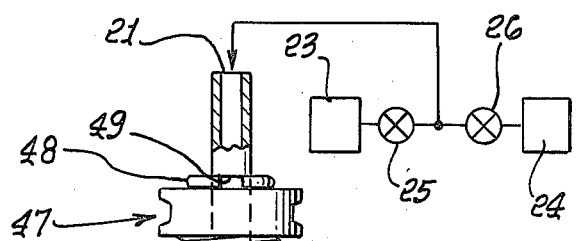
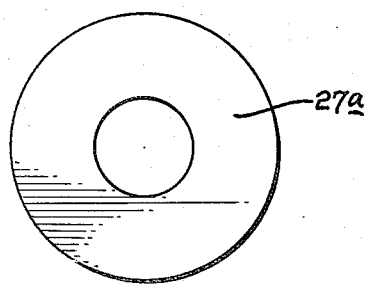
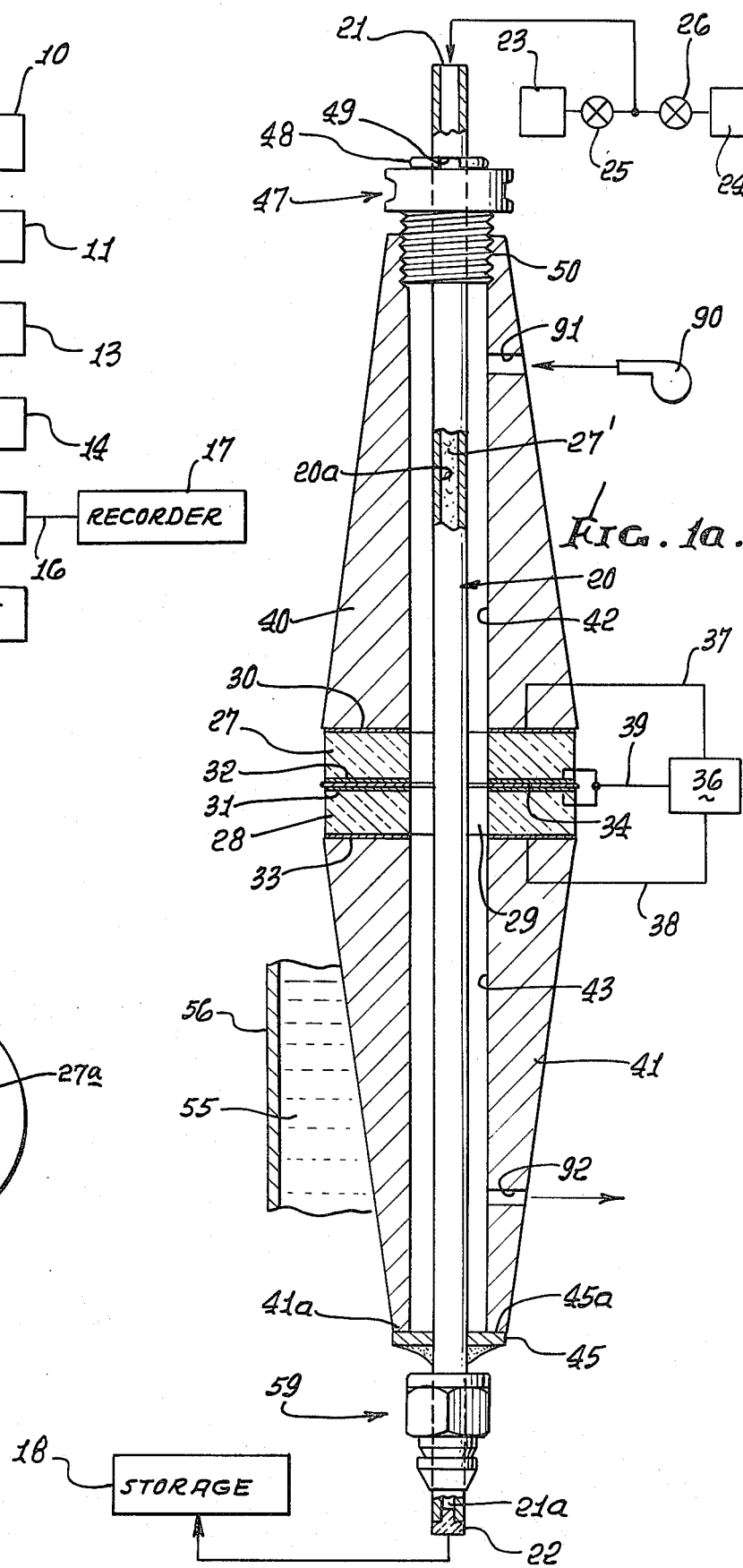

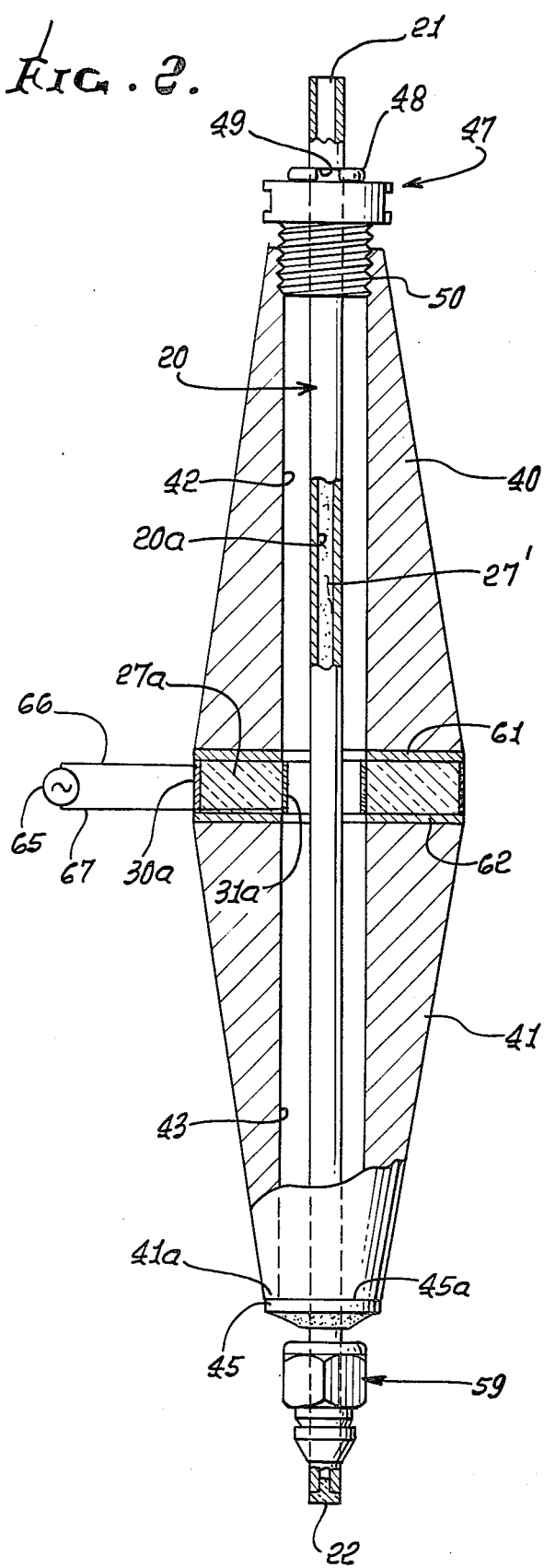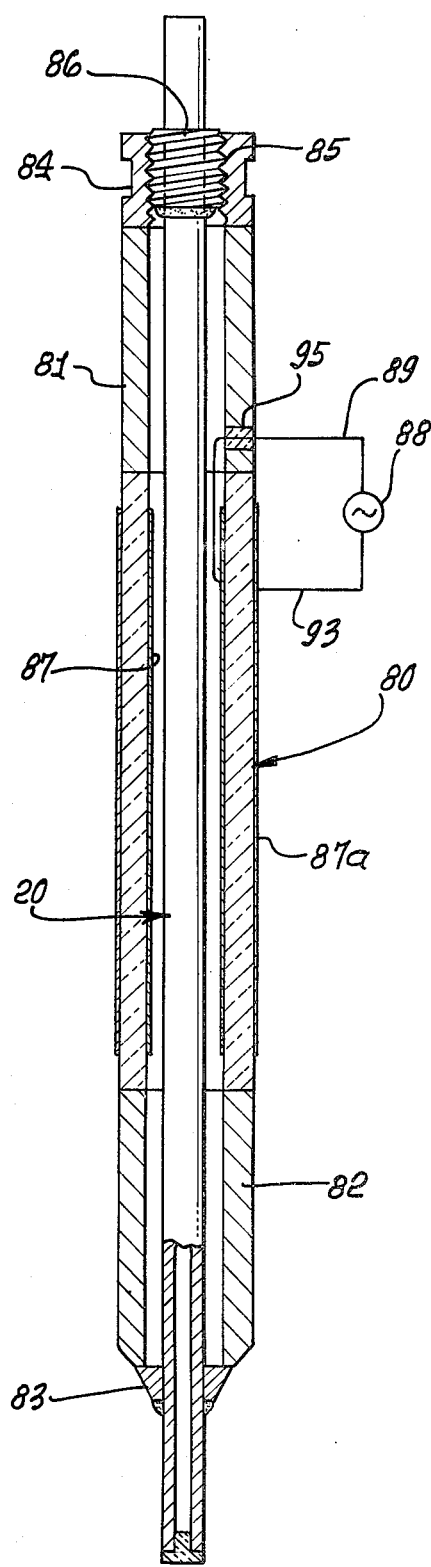

CHROMATOGRAPHIC APPARATUS AND METHOD OF OPERATION

BACKGROUND OF THE INVENTION

The invention relates generally to chromatography, and more particularly concerns application of mechanical energy to chromatographic columns and packings.

Chromatography is a general term which has been applied to techniques useful in the separation of substances, which can be gaseous, liquid, or solid in nature. Generally, the separation is due to the sample partitioning between a liquid or solid stationary phase, and a progressively moving mobile phase, which can be gaseous or liquid in nature.

The stationary phase is captive in a tube of selected interior diameter and length, which is generally called a column, and can be provided with means for introducing the moving phase and the sample, at the head of the column. Sensitive methods of determining when the separated sample components appear in the column effluent, can be instrumented to produce an electrical signal.

If the mobile phase is a gas, the technique is called Gas Chromatography, and if a liquid, the term is Liquid Chromatography. For the latter, when the column is tightly packed with a micron size particulate material requiring high solvent pump pressures, the technique can be called H.P.L.C. or high performance liquid chromatography. Equipment employing H.P.L.C. is in extensive use for both analytical and preparative techniques, in industrial, biochemical, chemical, and medical fields.

The column is an essential component in such equipment, and is very difficult to pack with the solid stationary phase, so that a minimum of voids are present. The particle size range is usually between preferred limits, and packing is achieved by introduction of a fluid slurry, and very high pump pressures. A good packing density and discrete particle size distribution, are essential requirements for efficient separations.

Need exists for a means for packing a column using much lower pump pressures, with consequent less chance of change in the particle size distribution by mechanical abrasion.

In this regard, application of much lower energy levels, and at higher frequencies to the column during a chromatographic procedure, would greatly improve the resolution, and other desirable separation parameters. Retention times would also be reduced, and solvent pump pressures greatly lowered for the same type separation, leading to constructions of improved cost efficiencies.

SUMMARY OF THE INVENTION

It is a major object of the invention to provide method and means facilitating the filling of a chromatographic column with uniform density packing, and in such manner as to require lower pump pressures and reduction of particle size attrition. Other objects of the invention include the provision of method and means enabling use of the apparatus at a different energy level during a chromatographic separation, to improve resolution, theoretical plate reduction, shorter retention times, and other advantages as will be further described.

Basically, the method of treating packing in a chromatographic tube includes:

(a) vibrating the tube to produce tube oscillating displacement,
(b) and transmitting such tube displacement to the packing in the tube.

As will appear, vibration of the tube is typically effected during filling of the packing into the tube, and/or after such packing filling and during introduction of the sample into the packing to be analysed. The tube itself may be vibrated to produce generally radial oscillatory displacement, and specifically, the tube may be oscillated to produce lengthwise oscillatory displacement with corresponding resultant generally radial displacement of the tube and packing therein. Further, the tube may be tensioned during such displacement, and such tensioning may be adjusted to control the oscillating displacement transmitted to the packing to controllably disperse the particulate packing creating uniform density and reducing or eliminating voids. The sample may consist of a liquid or gas, and may be dissolved in a liquid solvent.

These and other objects and advantages of the invention, as well as the details of an illustrative embodiment, will be more fully understood from the following specification and drawings, in which:

DRAWING DESCRIPTION

FIG. 1 is a block diagram of chromatographic apparatus;

FIG. 1a is a vertical elevation, in section, showing one form of apparatus incorporating the invention;

FIG. 2 is a vertical elevation, in section, showing another form of apparatus incorporating the invention;

FIG. 3 is a plan view of a transducer, as incorporated in FIG. 2;

FIG. 4 is a vertical elevation, in section, showing yet another form of apparatus incorporating the invention;

DETAILED DESCRIPTION

Figure 5:
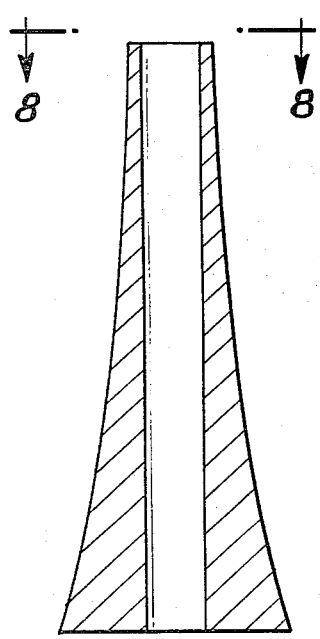
FIGS. 5–7 are vertical elevations showing different forms of coupling horns.

A modern chromatograph or chromatographic apparatus includes basic elements that may be manually operated, or automated, and computer or microprocessor controlled. The functional parts, however, remain the same with differences in sophistication. FIG. 1 illustrates the fundamental elements of a liquid chromatograph. A liquid reservoir 10 is connected to a pump 11, which is capable of essentially pulse free, high pressure delivery of the solvent at 12 with small flow rates and pressures, that may be as high as 6,000 psi.

For certain procedures, it is desirable to have several solvent streams of different compositions, which can be blended.

In such an event, several reservoirs are employed, and an equivalent number of pumps which can be interconnected to facilitate delivery of a mixed solvent stream, of variable, and controllable composition. Such a technique is called "Gradient" chromatography, and when a single solvent is used, the method is called "Isocratic". In any case the solvent stream is introduced to an injection port, which is so designed that a small sample can be introduced into the stream, without any essential interruption of the flow.

The sample is normally introduced as by injector 13 at the head of the column 14, and can be visualized as a small slug appearing in a smooth flowing stream of solvent. The column is typically a smooth bore, small diameter, length of high pressure tubing, with suitable high pressure fittings at each end, with low turbulence introduction and exit for the solvent. The column is filled with a tightly packed, very specific material for the separation desired, the packing being held in position at its lower end by a microporous frit to prevent packing loss, but through which solvent can pass readily.

Separation of the sample components takes place by partitioning on the packing, and the intention is that components appear at the far end of the column in the solvent stream, but as sharply separated fractions.

The column effluent is passed through a detector 15 which can be specific to the chemical or physical character of the particular sample. Detector sensitivity may be characterized by changes in refractive index, infrared, ultraviolet, or visible monochromatic absorbance, electrical conductivity, fluorescent optical shifts, and other phenomena capable of detecting, and quantitatively determining the change in the solvent stream by the separation components. Detector output signals at 16 can then be recorded, integrated, and otherwise manipulated as at 17 to produce useful information as a function of retention time, measured from the time of injection of the sample. Effluent storage is indicated at 18.

Column size and packing are determined by the purpose of the separation. A preparative column is used where separation of substantial quantities of a compound are required for further use.

Such a column may typically have up to 2 inches diameter, with a packing loading between 0.5 to 10 grams, and packing particle size of 100 to 200 microns. The solvent flow would typically be between 50 to 100 ml. per minute. Smaller flow rates, column diameters, and particle sizes of packing, are proportioned according to need. A typical analytical column might have a column diameter of 2 to 5 m/m and a length of 10–25 cm., packing weight of 0.5 to 2 grams, and solvent flow rate between 1 and 10 ml./mt.

Column packings are highly specialized to a particular chemical composition, and the type of separation procedure required. Packing technology can be divided into two general areas. The first is where molecular distribution information is required for high molecular weight compounds, and the physical separation is performed with discrete pore size packing. This is called size exclusion chromatography and the packing is normally a microporous polymer. Here, the lower molecular weight fractions can enter the pores of the packing, while the larger molecules cannot, and, therefore, elute first. The lower molecular weight fractions are retained for periods depending on the shape, and relative size, of the fraction, and the pore size.

The other general technique employs packings made of silica, or alumina, in particle sizes between 5 and 10 microns which are usually hard and impervious, or with controlled porosity. Specific chemical modification of the particle surface provides means for partition of chemical species passing in the solvent stream. There are no absolutes of specificity, however, and it is clear that several separation processes in any column must occur simultaneously.

An understanding of the invention requires further description of presumed mechanisms of separation, than the general description given so far. Some descriptive terms are as follows:

PARTITION (NORMAL PHASE)

The packing surface is coated with a stationary organic phase which is usually polar, and may have nitrile, diol, or amino pendant groups. The mobile phase is selected on the basis of elution strength, such as the increase in a higher series of solvents where a hydrocarbon is low, and water has a high eluotropic strength.

REVERSE PHASE PARTITION

The stationary phase is non-polar, with pendant C8 or C18 hydrocarbon chains. The eluotropic strength of the mobile phase is in the reverse order for the normal phase. This technique is presently the most useful in general application for analytical procedures, because of ease of separation of compounds of any polarity. The solubility properties of the compound are considered when the stationary and mobile phase are selected. A mixture of solvents can be used whose composition may be gradually changed during analysis.

ION EXCHANGE

This is rather more difficult in technique than most others. The stationary phase is ionic in nature, and bonded to a non-functional matrix such as silica. The mobile phase consists of aqueous buffers.

ABSORPTION CHROMATOGRAPHY

Absorption chromatography is one of the oldest types of liquid chromatography. Stationary phases are silica, or alumina. Silica gel is commonly used, and retention and selectivity are the result of silanol groups on the surface, interacting with polar or functional groups on the solute molecules. Solutes that are non-polar, and very polar water soluble compounds, do not develop good separation. Intermediate or alcohol soluble compounds can show good resolution.

Separation is based on differences in energy of absorption of sample components on the stationary phase. Mixtures of solvents are used as the mobile phase for controlled selectivity.

Generally one can say that improvement of efficiency in separation shows up as decrease in the width of the eluted band. Resolution depends on the narrowness of the peak, and retention time between peak maxima. The former is due to column efficiency and the latter to selectivity. From a practical viewpoint, the recorded peak shapes of separated components can be assumed to be Gaussian in contour. Deviations from the idealized shape such as increased peak width, assymetry, tailing, and other phenomena are symptomatic of packing variations, for a set of conditions, where flow rates, sample size, chemical species of the interreacting components are well known, and idealized.

Using a known packing proven as to separation efficiency in a suitable system by chromatography, increased efficiency in an improved column would be demonstrated by peak width reduction, provided means are available to achieve an improved packing density, with uniform transverse, and longitudinal distribution, of the particles. In this regard, bridging, which causes small cavities, and lower density of the packing along the walls, due to friction and other effects, is difficult to avoid during manufacture, and is responsible for efficiency differences from one column to another, packed with the same material.

A numerical value which is commonly employed to describe quality in a column is Height Equivalent to a Theoretical Plate (H.E.T.P.), "h" a concept taken from chemical engineering to describe the efficiency of a distillation column. Actually, there are no plates in a chromatographic column, but a theoretical plate is a section of the column in which the stationary and mobile phase are in equilibrium. Obviously, since a large number of plates are desirable for resolution, the value of "h" should be as small as possible. Thus the number of theoretical plates in a column length will characterize the quality of the column.

A measure of the theoretical plates available in a particular column can be made by the measurement of the parameters of a particular peak.

$$N = 5.54(tr/w_{\frac{1}{2}})^2 \qquad (1)$$

N = number of theoretical plates
Tr = retention time at peak apex
$w_{\frac{1}{2}}$ = half height peak width Plate height "h" is affected by mobile phase flow velocity, multiple, path, eddy diffusion, channelling, and other factors attributed to packing efficiency and particle size.

Improvements in column packings have indicated that good performance can be obtained by the use of shorter lengths, smaller diameters, and smaller particle sizes in analytical columns. Since the column packings are very expensive, and increase in price in relation to the reduction in particle size, an economic advantage is to be sought by use of smaller packing volume. Since chromatographic solvents are expensive, the smaller bore columns require lower flow rates and cost savings can be attained. Smaller diameter columns and smaller diameter particles, however, create greater difficulty in producing the desired small theoretical plate height.

Typically, an analytical column would be prepared from high pressure tubing, with a polished bore between 1 and 4 mm., diameter, and 25 cm., long. A fine porous frit plug is inserted at the effluent end, and high pressure fittings attached at the tube extremities. With particle size packings of 10 microns or smaller, a wet slurry method must be employed. The packing weight would be between 0.5 and 2 grams for silica.

A high viscosity, or high density liquid is necessary to produce a fluid slurry, and to prevent sedimentation. The packing liquid must not react with any coatings on the particles, nor be irreversibly absorbed. A typical material of high viscosity would be cyclohexanol which is mixed with the silica, degased, and placed in a small tube at the head of the column. A high pressure pump then is used to pump more cyclohexanol and the slurry into the bore of the empty column, and pulsed to compact the packing. The pressures used should be in excess of the anticipated mobile phase pressure during use. The cyclohexanol is then washed off the packing by a sequence of low viscosity solvents pumped through the column by the high pressure pump.

This procedure requires very high pressures, usually 10,000 psi and more, and tends to fragment the discrete particles by attrition, and the production of a good column can be difficult art, rather than a science.

As referred to above, one of the purposes of the present invention is the design, and use of a unique device which permits the filling of a chromatographic column to a uniform density. Furthermore, lower pump pressures are required, and particle size attrition greatly reduced.

A second purpose of the invention is to use the device at a different energy level during a chromatographic separation, to improve resolution, theoretical plate reduction, shorter retention times, and other advantages which will be further described.

DESCRIPTION OF THE APPARATUS

The general purpose of the present invention is to provide agitation in a controllable manner, along the length of the column during a packing procedure. After packing is completed, the level of vibration is greatly reduced, to provide or enable rapid solvent and sample throughputs.

The problem involves the application of ultrasonic energy along the length of a rigid tubular column, so that the fundamental frequency is essentially sinusoidal, and of controllable frequency and amplitude. To this end, the column is pretensioned along its length, and piezoelectric or magnetostructive elements are so located and excited as to typically produce a standing wave along the tube. To prevent axial flexure, or unwanted longitudinal vibrations, the excitation means are preferentially arranged in coaxial relation with the tube length. The use of piezoelectric, or magnetostrictive elements as high frequency excitation means, involves practical constraints of matching the physical size of the transducer with the desired excitation length of the column.

For the purpose of providing considerable vibration in the column length during packing, it is desirable that the amplitude of the energy waves at the end of the column be substantial. Practical high energy transducers currently employed in industry and for sonic applications are usually ceramic anisotropic crystals of varying compositions. High Curie point materials practical for industrial uses include Barium Titanate, Lead Titanate, or Lead Zirconate (or combinations thereof) with some minor additions to change some properties. Because of the ceramic nature of these materials, they can be made in almost any shape consistant with shrinkage and cracking losses, that occur in thick structures.

Referring to a specific embodiment as shown in FIG. 1a, an elongated chromatographic tube 20 has an inlet 21 at its upper end, and an outlet 21a at its lower end. A porous glass or ceramic frit plug 22 may be located at and adherent to that lower end to retain or support packing in the metallic tube, the packing being particulate to disperse a liquid or gas sample to be analysed. Means for flowing packing into the tube is shown at 23, and means for flowing a sample into the packing appears at 24, suitable valves indicated at 25 and 26. Packing in the tube appears at 27'.

Means is operatively coupled to the tube for producing tube oscillatory motion or displacement that is transmitted to the packing, as for example during flow of the packing particles into the tube, or after their reception in a column within the tube bore 20a. Typically, such means takes the form of transducer apparatus for imparting lengthwise oscillation to the tube 20, and resulting in corresponding radial oscillation of the tube (by Poisson's ratio consideration) which is in turn transmitted to the packing 27' to uniformly disperse or distribute same across the tube bore area. The transducer apparatus in FIG. 1a takes the form of two like discs 27 and 28 which extend about the tube and are spaced therefrom at clearance 29. Such tranducers discs may be piezoelectric and may consist of barium, lead, strontium titanate, or zirconate, or other functionally equivalent ceramics with silvered flat surfaces at 30–33, and a conductive (as for example copper) sheet 34 may be interposed between surfaces 31 and 32, as shown. A source of A.C. power is shown at 36, with leads 37 and 38 connected to surfaces 30 and 33 to apply high voltage of one changing polarity to those surfaces. Lead 39 is connected to surfaces 31 and 32 to apply high voltage of opposite changing polarity to such surfaces; accordingly, the discs expand and contract, in oscillatory alternation, and at high frequency, in the direction of the tube length or axis. Magnetostrictive transducers may alternatively be used (see U.S. Pat. No. 2,566,984). Surfaces 30 and 33 may be insulated from members 40 and 41.

Also provided is coupling structure extending between the tranducers and opposite end portions of the tube. In the example, such structure takes the form of like, equal length metallic members 40 and 41 which taper toward opposite ends of the tube. Such members are tubular and have bores 42 and 43 to pass tube 20, as shown. Retaining means is provided to couple the members to the tube to place the members and transducers in compression and the tube in tension. As shown, the retaining means includes a support ring 45 attached to the tube lower end portion as by welding or brazing. Its upper surface 45a supports the reduced end 41a of member 41. Likewise, an upper retaining nut 47 is retained axially on the tube by a ring 48 received in a tube groove 49. The nut has threaded interengagement at 50 with the bore of the upper member 40, whereby rotation of the nut adjusts the axial compression in the members 40 and 41 and the transducers 27 and 28, as well as the tension in the tube 20.

A high pressure fitting is provided at 59 on the tube lower end portion, and supports frit plug 22.

Both flat sides of the discs which are covered with a conductive coating such as silver as described may be polarized by well known methods. Useful resonant frequencies are between 18 KHz and 100 KHz, and since the dynamic driving force of a half wave length transducer is efficient mainly in the center, the end positions are essentially inert. The mechanical quality factor "Q" can be optimized by the use of metallic members 40 and 41 or other energy transfer means. The members 40 and 41 are elongated and symmetrical in shape and mass on each side of the transducer.

Figure 6:
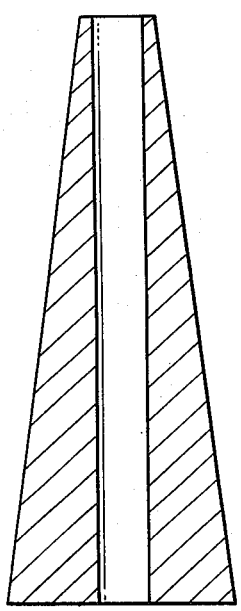
Figure 7:
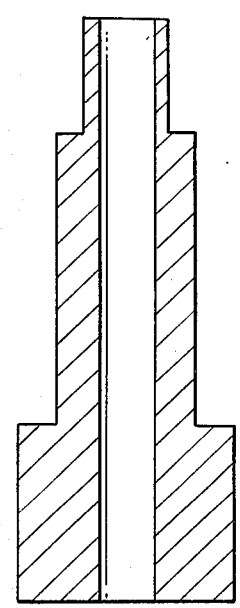
Figure 8:
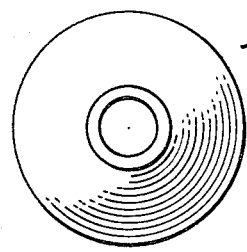
FIG. 8 is a plan view on lines 8—8 of FIG. 5.

By providing a tapered structure to the end cap members 40 and 41, which can be exponential, flat taper or step reduction in design, the small mechanical movement of the transducers can be increased by a maximum factor of about eight for both members, or generally within limits as a function of the difference in area between the transducer ends, and the drive ends of the members coupled to the column or tube 20. See the exponential member of FIG. 5; the straight tapered member of FIG. 6; and the stepped member of FIG. 7.

By using a plurality of transducer discs in the form of a stack, with correct attention to polarity, further increase of the dynamic movement of the column can be obtained. Other shapes and types of transducers are practical for the invention, such as piezoelectric right cylinders which are poled and excited across the cylinder wall. The metal end members are then attached to the ends of the cylinder, which move in the longitudinal mode.

Also usable are ferroelectric transducers formed as tubular stacks, with permanent magnetic poles.

Because the energy input to the member terminations, and column, as well as mechanical and electrical losses in the transducer, generates heat, means for controlling the temperature can be provided. Such means can be in the form of a circulating temperature controlled fluid in contact with the column, and/or metal horns, or by the forced circulation of air through the structure. See for example coolant 55 adjacent member 41, and within shell 56, and air circulation by blower 90 and via ports 91 and 92 to cool tube 20.

Temperature control of the column during use is an important factor in reproducibility, and can be achieved in various ways. One way is to control the temperature of the solvent liquid delivered from source 24, the latter also exemplifying such a control (achieved by an electrical heater for example).

Referring now to FIG. 2, elements shown corresponding to those in FIG. 1a are given the same numbers. Instead of two transducers, only one is employed and is shown at 27a. It is in the form of a disc extending about the tube 20 at a location half way along the length of the latter, and may consist of piezoelectric material. Its inner and outer circular walls are silvered at 30a and 31a to provide electrodes. Mica or other suitable insulation is provided at 61 and 62 between the disc and the large ends of members 40 and 41, to transmit compressive force lengthwise of the tube axis. A source of high frequency electrical power is indicated at 65, with leads 66 and 67 extending to the two electrodes. Power induced radial expansion and contraction of the disc results in axial contraction and expansion of the disc and transmission of such oscillation to members 40 and 41, with amplified displacements of their smaller ends, transmitted to the tube. The latter expands and contracts, lengthwise, and produces resultant radial expansion and contraction transmitted to the packing and/or the sample in the packing, as described above.

Referring to the FIG. 4 modification, the chromatographic tube 20 extends through an elongated, cylindrical piezoelectric transducer 80, and through two cylindrical metallic coupling members 81 and 82. The latter are retained between a lower retainer 83 welded to the tube lower portion, and an upper retainer 84 in the form of a nut. It is thread connected at 85 to a boss 86 which is in turn connected as by welding to the tube upper portion. Adjustment rotation of the nut tensions the tube, the transducer 80 and members 81 and 82 thus being held in compression between the retainers. The inner and outer walls of the cylindrical transducer bear silver electrodes 87 and 87a to which A.C. power is transmitted from source 88 via leads 89 and 93. Note insulated bushing 95 via which lead 89 has access to the inner electrode.

Figure 9:
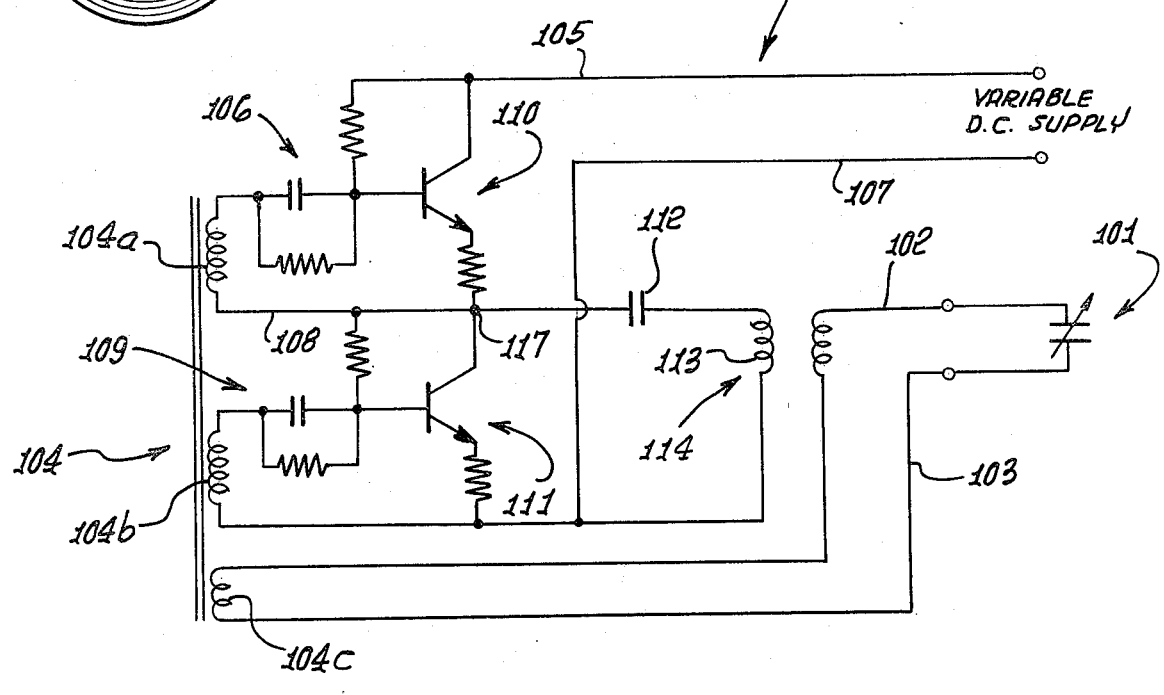
FIG. 9 is a power circuit diagram.

FIG. 9 illustrates a power drive circuit 100 for the transducer or transducers. The latter is shown at 101 in the form of a variable capacitor. Leads to the latter are shown at 102 and 103, connected to winding 104c of ferrite transformer 104. One tap of winding 104a is connected with a variable DC supply via lead 105 and RC network 106. The other lead 107 of the supply is connected with one tap of winding 104b. The other tap of winding 104a is connected to junction 117 via lead 108, and the other tap of winding 104b is also connected to junction 117 via RC network 109. Transistors 110 and 111 are connected as shown, to conduct in alternation, whereby matching AC is supplied via the point 117 and capacitor 112 to winding 113 of matching transformer 114. The other winding of transformer 114 is connected in series with lead 102.

EXAMPLE

A small volume liquid pump capable of delivering pressures up to 12,000 lbs. is fitted with an inlet reservoir and pressure gage on the outlet manifold. High pressure tubing and valving allow the liquid stream to be diverted to a thick walled capsule with an inlet and outlet fitting, and electromagnetic stirring means. The capacity of the capsule is several cubic centimeters.

The outlet fitting is attached to a 20 cm long length of stainless steel tubing (corresponding to tube 20) with a 2 micron frit filter at the far end. The tube is 4.6 millimeters in bore diameter. High pressure tubing fittings are provided at each end. The previously described ultrasonic transducer, and tapered horns are attached near the end of the tube and tightened, so that the transducer is under compression and the tube under tension.

The capsule is loaded with a 10% degassed packing slurry of 15 micron silica gel and cyclohexane, and the magnetic agitator turned to keep the silica in suspension. The pump reservoir is filled with degassed cyclohexane, and the pump turned on at a flow rate of 6 ml/minute.

The initial pressure was low, but built up to 5,000 psi as the column became packed to a higher density. The time to peak pressure was 45 minutes.

The column was then emptied and the same experiment was performed but with power on the transducer. By measurement, the fundamental driving frequency was 35 KHz and the power level in the transducer 1,200 Watts.

The pump was turned on, and at the same flow rate and conditions, and the pressure increased to 4,800 psi peak in 15 minutes. This indicates that the new packing method is faster, and capable of high packing density. At lower solvent flow rates, the pump head pressure dropped to about 2,800 psi at 2 ml. per minute.

Various samples may be efficiently treated using the above apparatus. It is contemplated that isotopes of Uranium can be separated efficiently and quickly, using the method and apparatus described.

I claim:

1. The method of treating packing in a chromatographic tube, the packing adapted to disperse a sample to be analysed, the steps that include:
   (a) vibrating the tube to produce tube oscillating displacement,
   (b) and transmitting said tube displacement to said packing in the tube.

2. The method of claim 1 wherein said vibration of the tube is effected during filling of the packing into the tube.

3. The method of claim 1 wherein said vibration of the tube is effected after filling of the packing into the tube, and during introduction of the sample into the packing, to be analysed.

4. The method of claim 3 wherein said sample includes Uranium isotopes in a liquid.

5. The method of claim 1 wherein the packing includes particulate to be vibrated in response to said transmission of tube displacement into the packing.

6. The method of any one of claims 1–3 or 5 wherein the tube is vibrated to produce generally radial oscillatory displacement thereof.

7. The method of any one of claims 1–3 or 5, wherein said vibration is carried out to effect generally lengthwise oscillatory displacement of the tube which results in corresponding generally radial oscillatory displacement of the tube wall.

8. The method of claim 7 which includes tensioning the tube during said lengthwise oscillatory displacement thereof.

9. The method of claim 7 including adjusting said tensioning of the tube to adjust the oscillatory displacement transmitted to the packing.

10. The method of claim 7 wherein said oscillation is transmitted to the tube via opposite ends thereof.

11. The method of claim 1 wherein the sample is in a liquid.

12. The method of claim 1 wherein the sample is dissolved in a liquid solvent.

13. The method of treating packing in a chromatographic tube, the packing adapted to disperse a sample to be analysed, the steps that include
    (a) producing oscillatory displacement, and
    (b) transmitting said displacement into the packing, in the tube.

14. The method of treating a sample in a chromatographic tube which contains packing to disperse the sample, the steps that include
    (a) producing oscillatory displacement, and
    (b) transmitting said displacement into the sample in the packing, in the tube.

15. In combination with a chromatographic tube for packing adapted to disperse a sample to be analysed,
    (a) means operatively coupled to the tube for producing tube oscillatory displacement transmitted to said packing.

16. The combination of claim 15 including means flowing the packing into the tube.

17. The combination of claim 16 including means flowing the sample into the packing in the tube.

18. The combination of claim 17 including means controlling the temperature of the sample in the packing.

19. The combination of claim 15 wherein said means includes transducer apparatus imparting lengthwise oscillation to the tube, and resulting in corresponding radial oscillation of the tube which is transmitted to the packing.

20. The combination of claim 19 wherein said means includes coupling structure extending between said transducer apparatus and opposite end portions of the tube.

21. The combination of claim 20 wherein said transducer apparatus extends about the tube, and said coupling structure includes a pair of coupling members respectively tapering toward opposite end portions of the tube, each member being tubular.

22. The combination of claim 21 including retaining means coupling said members to the tube to place said members and said transducer apparatus in compression and said tube in tension.

23. The combination of claim 22 wherein one of said retaining means is adjustable to controllably vary said tension and said compression.

24. The combination of claim 22 including an electrical power source to transmit AC power to said transducer apparatus causing oscillatory displacement thereof in the direction of the tube length.

25. The combination of claim 19 wherein said transducer apparatus comprises at least one piezoelectric disc extending about the tube.

26. The combination of claim 19 wherein said transducer apparatus comprises at least one magnetostrictive disc extending about the tube.

27. The combination of claim 19 wherein said transducer apparatus comprises a piezoelectric disc held in compression between said members, the inner and outer walls of the disc provided with electrodes to which high frequency power is transmitted.

28. The combination of claim 19 wherein said transducer apparatus comprises two piezoelectric discs which are stacked between and held in compression by said members, the opposite faces of the discs provided with electrodes to which high frequency power is transmitted.

* * * * *